United States Patent [19]
Townsend

[11] Patent Number: 5,495,752
[45] Date of Patent: Mar. 5, 1996

[54] EROSION DETECTOR FOR A FEED WATER STEAM NOZZLE

[76] Inventor: Johnnie V. Townsend, 20230 Marx, Detroit, Mich. 48203

[21] Appl. No.: 382,088

[22] Filed: Feb. 1, 1995

[51] Int. Cl.⁶ .................................................. G01N 17/00
[52] U.S. Cl. .................................................. 73/86
[58] Field of Search .................................................. 73/86

[56] References Cited

U.S. PATENT DOCUMENTS

| | | |
|---|---|---|
| 4,305,278 | 12/1981 | Stewart et al. . |
| 4,339,945 | 7/1982 | Knudsen et al. . |
| 4,644,780 | 2/1987 | Jeter . |
| 4,732,004 | 3/1988 | Brand et al. .............................. 60/646 |
| 4,776,170 | 10/1988 | Blangetti .................... 60/689 |
| 4,922,748 | 5/1990 | Hopenfeld . |
| 4,945,343 | 7/1990 | Rodriguez . |
| 5,353,653 | 10/1994 | Watanabe et al. . |
| 5,377,533 | 1/1995 | Shaw et al. .................................. 73/86 |

*Primary Examiner*—Hezron E. Williams
*Assistant Examiner*—Jay L. Politzer
*Attorney, Agent, or Firm*—Peter D. Keefe

[57] ABSTRACT

A feed water steam nozzle erosion detector composed of an erosion detection pipe alongside and immediately adjoining the feed water steam nozzle, and at least one sensor connected with the erosion detection pipe to detect that the erosion of the feed water steam nozzle has proceeded to the point of eroding into the erosion detection pipe. It is preferred that three sensor modalities be provided. A temperature sensor detects a rise in temperature occasioned because of steam entry into the erosion detection pipe. A metal fragment sensor detects the presence of metal fragments associated with the erosion of the erosion detection pipe and the feed water steam nozzle. A steam pressure sensor detects a build-up of steam pressure in the erosion detection pipe and further serves as a steam discharger with built-in pressure relief. Each of the sensors is associated with an electrical circuit which provides one or more signals to the boiler operator when erosion has been detected by the sensors.

22 Claims, 4 Drawing Sheets

EROSION DETECTOR FOR A FEED WATER STEAM NOZZLE

BACKGROUND OF THE INVENTION

1. Field of the Invention

The present invention relates to steam nozzles used to pre-heat feed water for steam based heating systems, and more particularly to a detector for detecting erosion of the steam nozzle so that replacement can be effected before damage can result.

2. Description of the Prior Art

In steam based heating systems, water is heated to steam and the steam is then delivered to various radiators of the steam pipe circuit for providing heating of a building, such as for example a school. In this regard, a boiler is used to heat feed water to steam. Cold feed water cannot be directly added to the boiler because if it mixed with the very hot environment inside the boiler, the result could be disastrous. Accordingly, feed water is pre-heated before being introduced into the boiler.

Pre-heating of feed water is carried-out by introducing a controlled flow of steam into the feed water of a feed water vessel via a feed water steam nozzle. The feed water steam nozzle has a number (usually four) of mutually spaced hole rows along its length (which is more-or-less about forty-five inches), each hole row having a plurality of regularly spaced apart (about one inch) holes (about one-quarter inch in diameter) along its length. Although made of heavy gauge metal (schedule 80, having a inner diameter of about two inches and an outer diameter of about two and one-quarter inches), the feed water steam nozzle is subject to erosion over its useful life because of the extreme steam pressures built-up inside. Indeed, the end of the feed water steam nozzle is capped at its distal end, so that steam entering into the feed water steam nozzle encounters returning steam from the distal end more-or-less around the mid-section of the feed water steam nozzle. Accordingly, the metal defining the holes slowly erodes away, the rate of erosion being highest at the mid-section portion of the feed water steam nozzle.

As the holes enlarge, the rate of steam release into the feed water is less controlled, and steam pulsations will occur. The result of these pulsations is "hammering", wherein the feed water steam nozzle shakes violently. When the feed water gets warmer, the "hammering" subsides, and the boiler operator, who has no exact knowledge of the condition of the feed water steam nozzle, might assume the problem was transitory and not the result of erosion. However, in all likelihood the steam water feed nozzle is dangerously eroded and presently in Hire need of replacement before major damage to the boiler system is sustained. However, boiler operators are reluctant to drain the feed water vessel and then go through the rigor of inspection on only the chance that the feed water steam nozzle is eroded.

Accordingly, it would be very beneficial if a definite indication of feed water steam nozzle erosion could be provided, especially before "hammering" occurs.

SUMMARY OF THE INVENTION

The present invention provides a definite indication of feed water steam nozzle erosion before "hammering" occurs.

The feed water steam nozzle erosion detector according to the present invention is composed of an erosion detection pipe alongside and immediately adjoining the feed water steam nozzle, and at least one sensor connected with the erosion detection pipe to detect that the erosion of the feed water steam nozzle has proceeded to the point of eroding into the erosion detection pipe.

It is preferred that three sensor modalities be provided. A temperature sensor detects a rise in temperature occasioned because of steam entry into the erosion detection pipe. A metal fragment sensor detects the presence of metal fragments associated with the erosion of the erosion detection pipe and the feed water steam nozzle. A steam pressure sensor detects a build-up of steam pressure in the erosion detection pipe and further serves as a steam discharger with built-in pressure relief. Each of the sensors is associated with an electrical circuit which provides one or more signals to the boiler operator when erosion has been detected by the sensors.

Accordingly, it is an object of the present invention to provide a detector of feed water steam nozzle erosion.

It is a further object of the present invention to provide a detector of feed water steam nozzle erosion using any or all of three sensor modalities.

It is another object of the present invention to provide a detector of feed water steam nozzle erosion using any or all of three sensor modalities, wherein a signal is rendered to alert a boiler operator before erosion has reached the condition that "hammering" would be experienced.

These, and additional objects, advantages, features and benefits of the present invention will become apparent from the following specification.

DETAILED DESCRIPTION OF THE PREFERRED EMBODIMENT

Figures 1, 2:
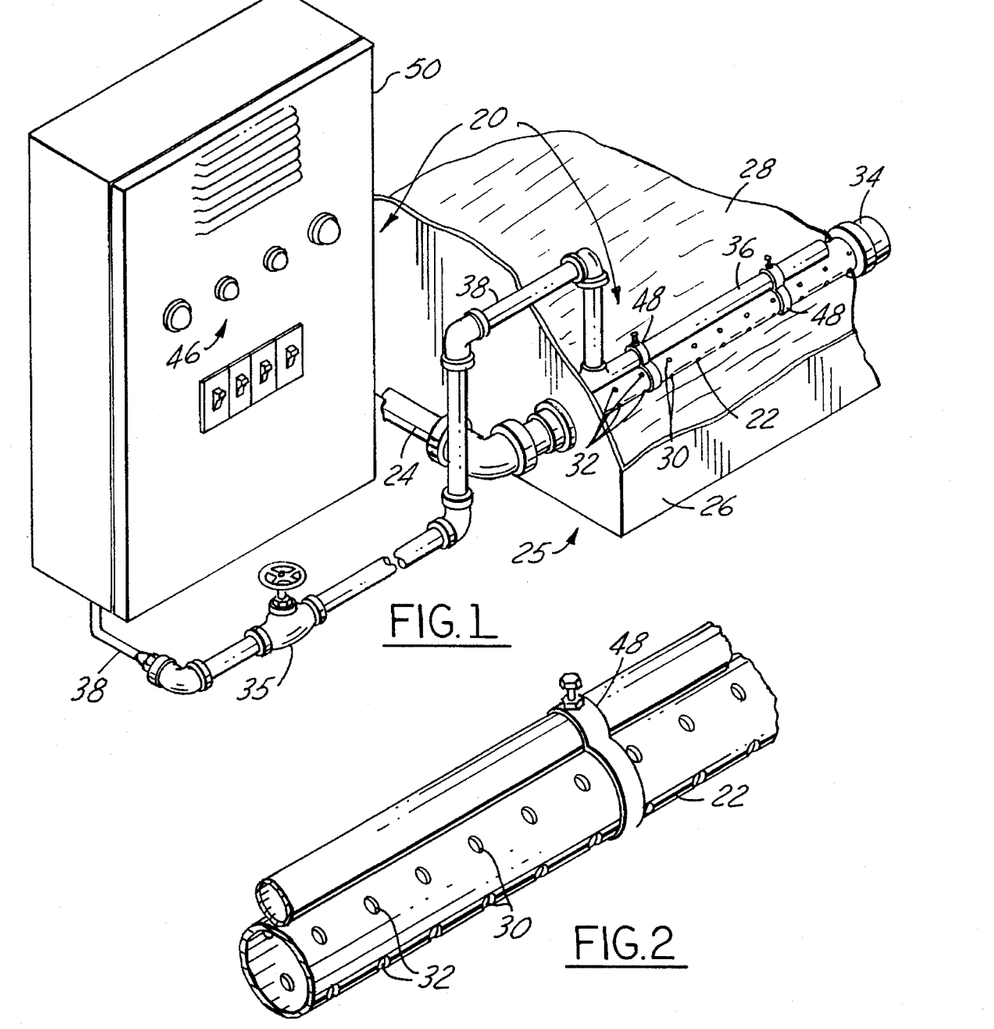
FIG. 1 is a perspective view of the feed water steam nozzle erosion detector according to the present invention, shown in operation with respect to a feed water steam nozzle and a feed water vessel.
FIG. 2 is a detail, broken away, perspective view of the erosion detection pipe of the feed water steam nozzle detector and the feed water steam nozzle of FIG. 1.
Figure 13:
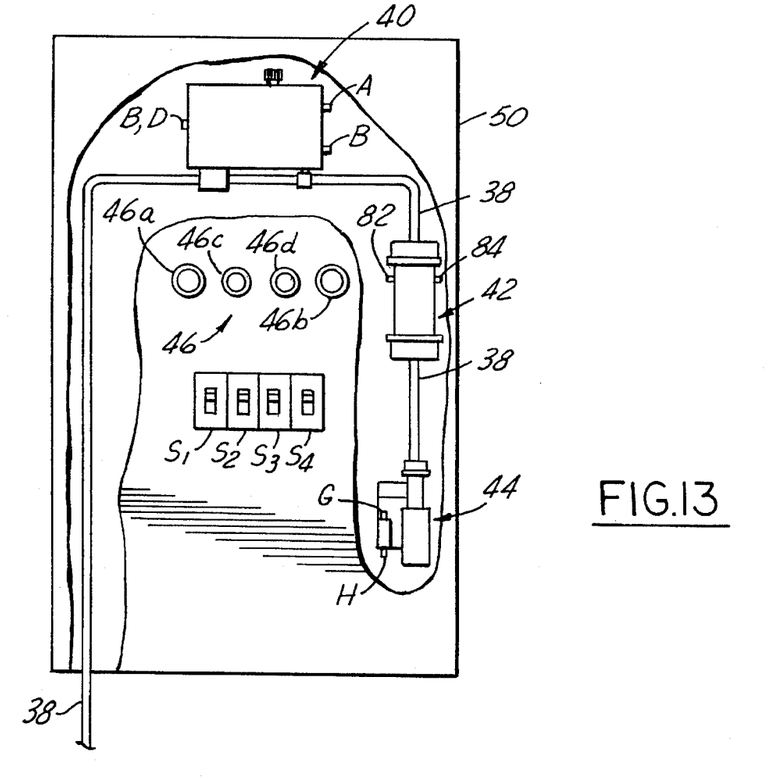
FIG. 13 is a partly sectional front view of the detection panel for the feed water steam nozzle erosion detector according to the present invention, showing the interconnection of the temperature sensor, metal fragment sensor, and the steam pressure sensor and steam discharger of the feed water steam nozzle erosion detector according to the present invention.

Referring now to FIGS. 1 and 13, the feed water steam nozzle detector 20 according to the present invention is depicted in operation with respect to a boiler apparatus 25 (shown in part). A feed water steam nozzle 22 is connected with a steam pipe 24 which is itself connected with a source of steam from a boiler (not shown) of the boiler apparatus 25. The feed water steam nozzle 22 is located inside a feed water vessel 26 of the boiler apparatus 25. Feed water 28 contained in the feed water vessel 26 is destined for later transfer to the boiler, wherein steam from the feed water steam nozzle 22 is used to pre-heat the feed water before transfer. The feed water steam nozzle 22 has a number of hole rows 30, each hole row having a plurality of regularly spaced holes 32 along its length. The feed water steam nozzle 22 is provided with a cap 34 at its distal end.

The feed water steam nozzle erosion detector 20 is generally composed of an erosion detection pipe 36 which is situated alongside and immediately adjoining the feed water steam nozzle 22, and at least one sensor connected with the erosion detection pipe via a conduit 38 to detect that the erosion of the feed water steam nozzle has proceeded to the point of eroding into the erosion detection pipe. In this regard, it is preferred that three sensor modalities be provided. A temperature sensor 40 detects a rise in temperature occasioned because of steam entry into the erosion detection pipe 36. A metal fragment sensor 42 detects the presence of metal fragments associated with the erosion of the erosion detection pipe and the feed water steam nozzle. A steam pressure sensor 44 detects a build-up of steam pressure in the erosion detection pipe and further serves as a steam discharger with built-in steam pressure relief. Each of the sensors is associated with an electrical circuit which provides one or more signal lamps 46 when erosion has been detected by the sensors.

A more complete description will now be undertaken, with reference being additionally directed to the remaining Figures.

As shown in FIGS. 1 and 2, the erosion detection pipe 36 is alongside in a parallel orientation with the feed water steam nozzle 22. To retain parallel orientation and adjoining proximity therebetween, one or more brackets 48 mutually engird the erosion detection pipe 36 and the feed water steam nozzle 22. The erosion detection pipe 36 has an interior space defined by a sidewall 36b and a sealed distal end 36a, and connects at its open other end to the conduit 38, which, itself, exits the feed water vessel 26 and enters into a detection panel 50 whereat the aforementioned sensors and signal lamps thereof are situated. The conduit 38 is provided with a shut-off valve 35, which allows selective closure of the conduit during an emergency situation or during times when the sensors 40, 42, 44 are being serviced. The shape of the erosion detection pipe 36 is shown being of a circular cross-section, however, another shape, such as a concave shape facing toward, and conforming to the curvature of, the feed water steam nozzle 22, is acceptable. The placement of the erosion detection pipe 36 is between two rows 30 or immediately next to at least one row so that as the holes 32 enlarge due to erosion, the steam also erodes the sidewall of the erosion detection pipe. Preferably, the erosion detection pipe 36 has a sidewall constructed of a schedule 80 metal (for example a three-quarter inch inside diameter and a one inch outside diameter) or another material having a preselected erosion resistance may be used, as will be discussed further hereinbelow.

Figure 3:
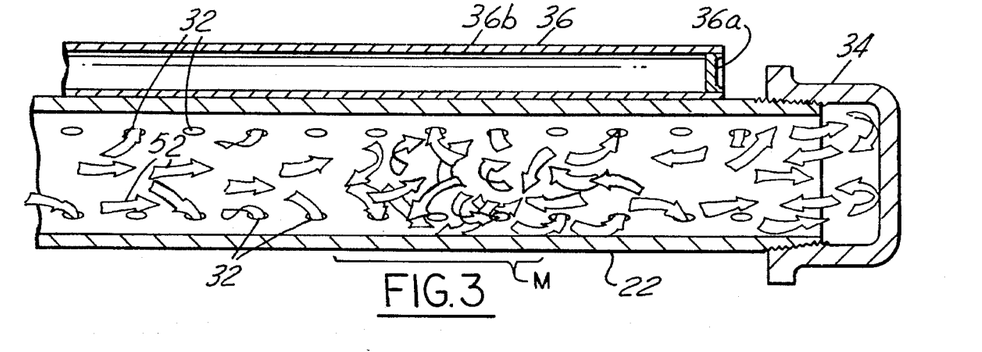
FIG. 3 is a sectional side view of a portion of the erosion detection pipe and the feed water steam nozzle of FIG. 1.

As shown in FIG. 3, steam 52 passes through the interior of feed water steam nozzle 22 and the flow of the steam becomes rather chaotic around the mid-section M of the feed water steam nozzle. Therefore, while steam 52 exits out of the feed water steam nozzle 22 via any of the holes 32, those at the mid-section M are subject to a more forceful release of steam. Accordingly, as a general rule of thumb, the holes 32 at the mid-section M are expected to erode faster than those nearer to either end of the feed water steam nozzle 22.

Figures 4, 5, 6, 7:
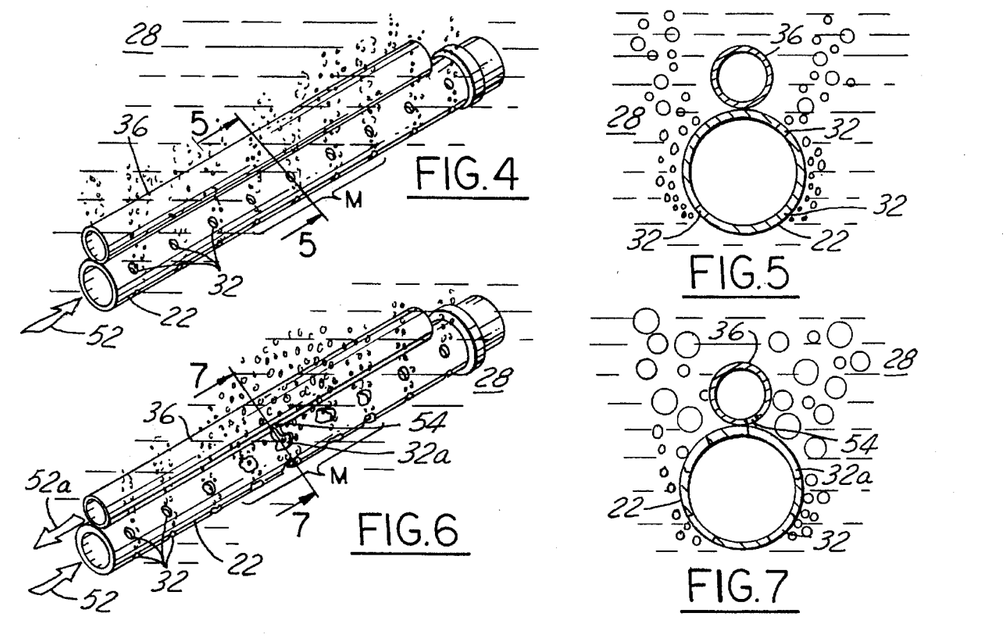
FIGS. 4 and 5 show, respectively, a perspective view and a sectional end view of the erosion detection pipe of the feed water steam nozzle detector and the feed water steam nozzle of FIG. 1, wherein little or no erosion has occurred.
FIGS. 6 and 7 show, respectively, a perspective view and a sectional end view of the erosion detection pipe of the feed water steam nozzle detector and the feed water steam nozzle of FIG. 1, wherein a detectable amount of erosion has occurred.

As shown in FIGS. 4 and 5, the release of steam 52 into the feed water 28 is generally uniform along the feed water steam nozzle 22 with the recognition that more steam may be released at the mid-section M due to the aforementioned internal dynamics of the steam within the feed water steam nozzle. This reasonably uniform release of steam 52 is beneficial and desirable because the feed water 28 is less agitated and the forces generated are generally spread-out so that nothing untoward (such as for example "hammering") would be expected. However, this uniform steam release is possible only provided the holes 32 are not unduly eroded.

As shown in FIGS. 6 and 7, the release of steam 52 into the feed water 28, is not uniform because holes 32 at the mid-section M of the feed water steam nozzle 22 have eroded into considerably larger sizes than the others. This means that steam is being released with great vigor at the midsection M, whereupon if the feed water is much cooler than the steam 52, pulsations can start-up in the feed water steam nozzle 22, and "hammering" can then ensue.

However, because of the feed water steam nozzle erosion detector 20, the boiler operator will become aware of the erosional state of the feed water steam nozzle 22 before "hammering" is noticed. This is because at least one of the holes 32a has eroded so much that the erosion has continued into the sidewall of the erosion detection pipe 36. In this regard, the preselected material of the sidewall of the erosion detection pipe 36 and the selected proximity thereof to the holes 32 yield a selected sensitivity of the erosion detection pipe to erosion of the holes 32 in the sense that the sidewall of the erosion detection pipe will develop a detectable opening therein responsive to a given extent of erosion of one or more of the holes in the feed water steam nozzle 22. As a result of the erosion into the sidewall of the erosion detection pipe 36, wherein an opening 54 is formed through which steam 52a, which may be carrying metal fragments, will now enter into the erosion detection pipe and then travel along the conduit 38 to the detection panel 50, whereupon the sensors 40, 42, 44 thereof will alert the boiler operator via the signal lamps 46.

The structure and function of the the sensors 40, 42, 44 and the signal lamps 46 associated therewith will now be detailed.

Figure 8:
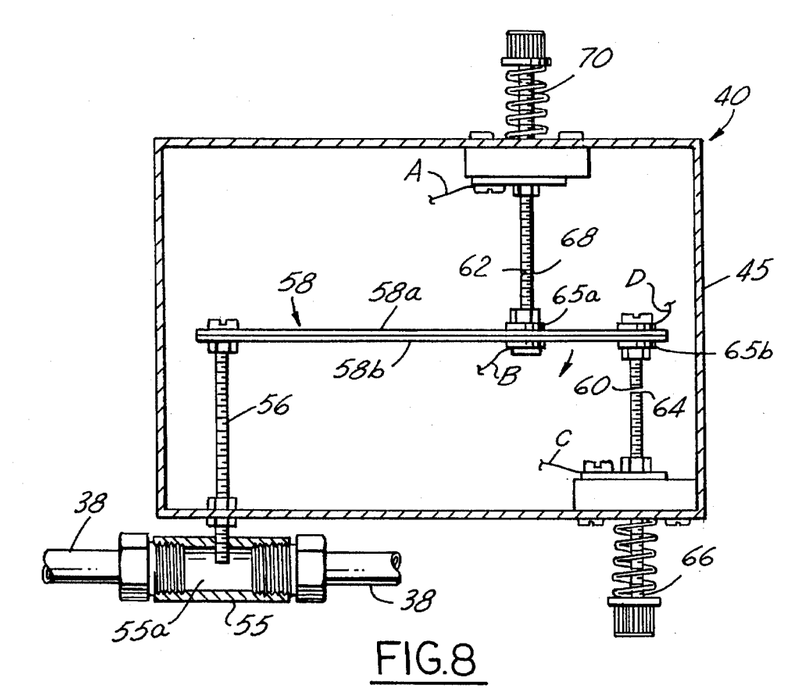
FIG. 8 is a partly sectional side view of a temperature sensor of the feed water steam nozzle erosion detector according to the present invention.

FIG. 8 depicts the temperature sensor 40 of the feed water steam nozzle erosion detector 20. The conduit 38 engages a coupling 55, and continues on past the coupling. A heat chamber 55a is formed inside the coupling 55, and a leg 56a of a threaded heat conductive shank 56 (such as for example a threaded steel shank) which connects with a temperature sensor housing 45 (wherein preferably the shank 56 is thermally insulated from the temperature sensor housing via one or more insulative spacers). The shank 56 is also connected with a bi-metallic strip 58 (such as one of brass 58a on one side and steel 58b joined thereto on the other side). A first contact 60 is provided on one side of the bi-metallic strip 56, and a second contact 62 is provided on the other side of the bi-metallic strip. Each of the first and second contacts are insulated from the bi-metallic strip. A third contact 64 is connected with the temperature sensor housing 45 and located in alignment with the first contact 60, wherein adjustment via a set-screw 66 provides for the relative adjustment of the spacing between the first and third contacts. A fourth contact 68 is connected with the temperature sensor housing 45 and located in alignment with the second contact 62, wherein adjustment via a set-screw 70 provides for the relative adjustment of the spacing between the third and fourth contacts. Each of the third and fourth contacts are insulated from the temperature sensor housing 45 by insulators 65a, 65b.

In operation, when steam 52a travels along the conduit 38 to the heat chamber 55a of the coupling 55, the leg 58a of the shank 58 will heat, as will the remainder of the shank, causing the bi-metallic strip 58 to heat. The third and fourth contacts 64, 68 are positionally adjusted so that under normal room temperature range, the bi-metallic strip causes the second and fourth contacts 62, 68 to mutually touch. However, heat released from the steam in the heat chamber 55a causes the bi-metallic strip 58 to bend so that the second and fourth contacts 62, 68 no longer touch, and the first and third contacts 60, 64 now mutually touch.

Figure 14:
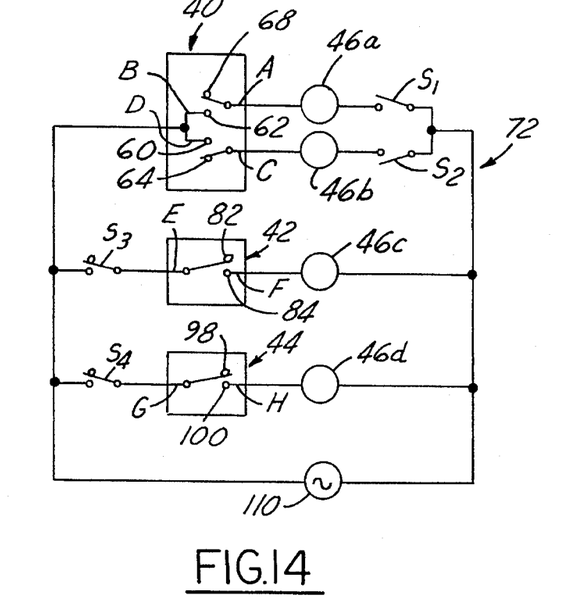
FIG. 14 is an electrical schematic for the temperature sensor, metal fragment sensor, and the steam pressure sensor, and the signal lamps thereof, of the feed water steam nozzle erosion detector according to the present invention.

When the second and fourth contacts 62, 68 mutually touch electrical wire A (which is connected to the fourth contact) and electrical wire B (which is connected to the second contact) form a closed circuit, and a green signal lamp 46a is lit via the electrical circuit 72 shown in FIG. 14. When the second and fourth contacts 62, 68 no longer touch, and the first and third contacts 60, 64 mutually touch, electrical wires A and B form an open circuit and electrical wire C (which is connected to the third contact) and electrical wire D (which is connected to the first contact) form a closed circuit, whereupon the green signal lamp 46a goes out and a red signal lamp 46b becomes lit, per the electrical circuit 72.

Figure 9:
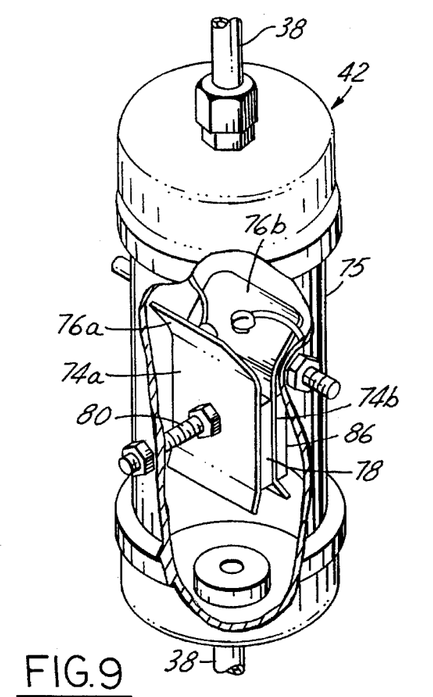
FIG. 9 is a partly sectional perspective view of a metal fragment sensor of the feed water steam nozzle erosion detector according to the present invention.
Figure 10:
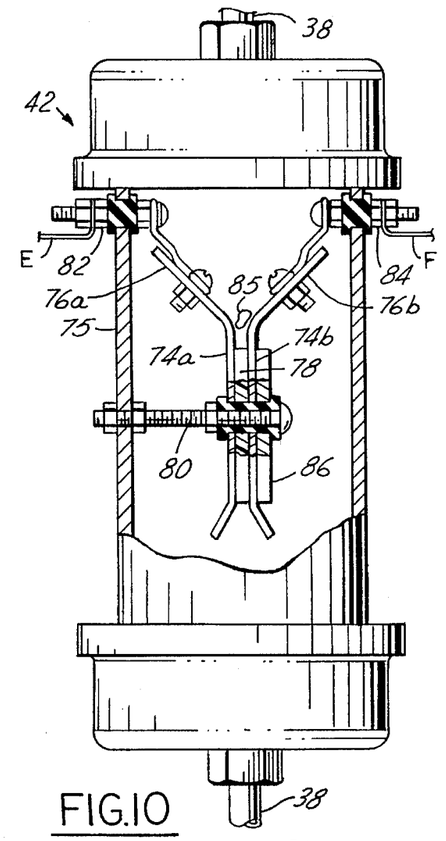
FIG. 10 is a partly sectional side view of the temperature sensor of FIG. 9.

FIGS. 9 and 10 depict the metal fragment sensor 42. In the event fragments of the metal of the sidewall of the erosion detection pipe 36 or the feed water steam nozzle 22 enter into the erosion detection pipe and are carried by the steam 52a along the conduit 38, these metal fragments will be detected by the metal fragment sensor 42. A metal fragment sensor housing 75 is provided having connections at opposing ends thereof to the conduit 38. Internal to the metal fragment sensor housing 75 are a pair of opposed plates 74a, 74b, each of which having flaired portions 76a, 76b at the upstream end thereof. The plates 74a, 74b are mutually separated by a thin spacer 78 that is electrically insulated with respect to the plates. A permanent magnet 86 is situated adjoining one of the plates 74b to thereby set-up a magnetic field between the plates that will assist capture between the plates of any metal fragments carried by the steam 52a. Alternatively, the permanent magnet 86 can be situated between the plates, thereby serving, itself, as the spacer 78, or a permanent magnet can adjoin each of the plates, respectively. The plates 74a, 74b, the magnetized spacer 78, and the permanent magnet 86 are connected to an electrically insulated standoff 80 which is connected, in turn, to the metal fragment sensor housing 75. A first lead 82 is connected with one of the plates 74a, and a second lead 84 is connected with the other of the plates 74b. The first and second leads are each insulated from the metal fragment sensor housing 75.

As shown at FIG. 10, if a metal fragment 85 enters into the metal fragment sensor 42, it will become lodged between the plates 74a, 74b, likely with the directional aid of the permanent magnet 86. The metal fragment 85 provides a conductive bridge between the plates 74a, 74b, whereupon electrical wire E (which is connected to the first lead) and electrical wire F (which is connected to the second lead) form a closed circuit, and signal lamp 46c will light, per the electrical circuit 72 of FIG. 14.

Figure 11:
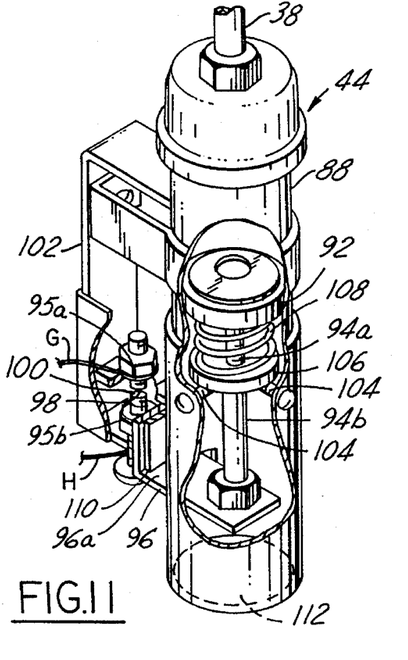
FIG. 11 is a partly sectional perspective view of a steam pressure sensor and steam discharger of the feed water steam nozzle erosion detector according to the present invention.
Figure 12:
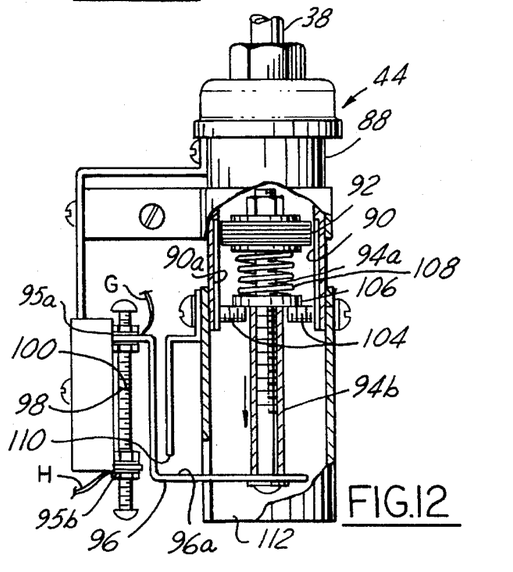
FIG. 12 is a partly sectional side view of the steam pressure sensor and steam discharger of FIG. 11.

FIGS. 11 and 12 depict the steam pressure sensor 44, which includes a steam discharger having built-in steam pressure relief. A housing 88 is provided which is connected to the conduit 38. Inside the housing 88 is a cylinder 90 and a piston 92 which is reciprocably movable therein side. The spacing between the piston 92 and the cylinder 90 is not air tight so that steam 52a can pass between the piston and the cylinder without undue pressure build-up in the conduit 38. This spacing provides steam discharge and some pressure relief of the steam 52a inside the conduit 38. Further steam discharge and pressure relief is provided by one or more grooves 90a axially formed in the cylinder which provide a steam by-pass when the piston has moved in the cylinder such as to expose them, as will be further discussed hereinbelow.

The piston 92 is mounted to a first rod 94a which, in turn, is threadably engaged with a second rod 94b. The second rod is mounted to an S-shaped flange 96. A fifth contact 98 is connected to the flange 96 and is electrically insulated therefrom by insulator 95a. A sixth contact 100 is connected to a bracket 102 and is electrically insulated therefrom by insulator 95b. The bracket 102 is, itself, mounted to the housing 88. Either, or preferably both, of the fifth and sixth contacts 98, 100 are positionally adjustable. Abutment bolts 104 are connected with the housing 88 at a lower end of the cylinder 90. A washer 106 abuts upon the abutment bolts 104, and a spring 108 is situated between the washer and the piston 92. The spring 108 biases the piston 92 upstream toward the conduit 38. An abutment member 110 is connected with the housing 88, and when it abuts a surface 96a of the flange 96 the resting location of the piston 92 under biasing of the spring 108 is determined.

In operation, as shown in FIG. 11, the position of the fifth and sixth contacts 98, 100 are adjusted so as not to mutually touch when the piston 92 is located at its resting location. However, as shown in FIG. 12, when steam 52a enters the housing 88 from the conduit 38, the steam will build-up pressure against the piston 92, eventually overcoming the biasing of the spring 108. Accordingly, the piston 92 will move against the biasing of the spring 108, whereupon the flange 96 also moves with the piston. As a result, the fifth contact 98 will touch the sixth contact 100, thereby closing a circuit defined by electrical wire G (which is connected to the fifth contact) and electrical wire H (which is connected to the sixth contact), which, per the electrical circuit 72 shown in FIG. 14, signal lamp 46d will light.

As can be understood from FIG. 12, when sufficient steam pressure in the cylinder 90 has moved the piston 92 sufficiently to allow the fifth and sixth contacts 98, 100 to touch, further amounts of steam pressure are relieved by the piston further moving against biasing of the spring 108 to now expose the grooves 90a whereby steam 52a can pass therethrough. Increasing steam pressure will cause the piston 92 to move further, exposing more of the grooves 90a, so that steam pressure inside the cylinder cannot reach a dangerous level. The steam will vent harmlessly out the open bottom 112 of the pressure sensor housing 88.

As indicated by the electrical circuit 72 of FIG. 14, a source of power 110, such as for example 110 V A.C. supplied by a utility company, powers the sensors 40, 42 and 44, as well as the signal lamps 46a, 46b, 46c and 46d. In this regard, switches $S_1$, $S_2$, $S_3$, and $S_4$ allow selective control over electrical connection of the source of power 110 to the sensors 40, 42, and 44 and the illumination of the respective signal lamps 46a, 46b, 46c, 46d in response thereto.

To those skilled in the art to which this invention appertains, the above described preferred embodiment may be subject to change or modification. For example, any of the three sensors 40, 42, 44 can be used individually, or in any combination with the others, wherein a steam discharger is used downstream thereof. Also for example, other signals, including audible or audible and visual signals can be used satisfactorily with the sensors to thereby warn the boiler operator of a dangerous state of erosion of the feed water steam nozzle. Such change or modification can be carried out without departing from the scope of the invention, which is intended to be limited only by the scope of the appended claims.

What is claimed is:

1. An erosion detector for detecting steam caused erosion of holes of a feed water steam nozzle and for signaling the detection of steam caused erosion, said erosion detector comprising:

erosion detection pipe means for receiving thereinto steam from an adjoining feed water steam nozzle, said erosion detection pipe means having a sidewall having a predetermined sensitivity to steam caused erosion, wherein steam is received into said erosion detection pipe means responsive to said sidewall being eroded by the steam;

conduit means connected with said erosion detection pipe means for providing a conduit for steam or steam borne metal fragments from said erosion detection pipe means;

sensor means connected with said conduit means for detecting at least one of steam and steam borne metal fragments in said conduit means to thereby provide detection of steam caused erosion of said sidewall of said erosion detection pipe means;

signal means connected with said sensor means for providing a signal that steam caused erosion of said sidewall of said erosion detection pipe means has been detected by said sensor means; and discharge means for atmospherically discharging the steam from said conduit;

wherein the detected steam caused erosion of said sidewall of said erosion detection pipe means is responsive to steam caused erosion of at least one hole of a feed water steam nozzle adjoining said erosion detection pipe means, wherein the detected steam caused erosion of said sidewall of said erosion detection pipe means is such that steam from the feed water steam nozzle enters into said erosion detection pipe means and thereupon passes into said conduit means.

2. The erosion detector of claim 1, wherein said sensor means comprises at least one of three sensor modalities comprising: temperature sensor means for detecting heat of steam carried in said conduit means from said detection pipe means, metal fragment sensor means for detecting metal fragments carried by steam in said conduit means from said detection pipe means, and pressure sensor means for detecting pressure caused by steam carried in said conduit means from said detection pipe means.

3. The erosion detector of claim 2, wherein said temperature sensor means comprises;

a temperature sensor housing connected with said conduit means;

heat sensitive means located in said temperature housing means for providing predetermined movement of said heat sensitive means with respect to said housing responsive to changes in temperature of said heat sensitive means caused by heat of steam carried in said conduit means from said detection pipe means; and means for conducting heat of steam carried in said conduit means to said heat sensitive means; and further wherein said signal means comprises:

electrical circuit means connected with said heat sensitive means for providing a first signal below a predetermined temperature responsive to movement of said heat sensitive means, and for providing a second signal above said predetermined temperature responsive to movement of said heat sensitive means.

4. The erosion detector of claim 3, wherein said heat sensitive means is a bi-metallic strip; said first signal is a green light; and said second signal is a red light.

5. The erosion detector of claim 2, wherein said metal fragment sensor means comprises:

a metal fragment sensor housing, said conduit means connecting with said metal fragment sensor at an upstream location and at a downstream location; and a pair of mutually spaced apart and mutually electrically insulated plates located within said metal fragment sensor housing; and further wherein said signal means comprises:

electrical circuit means connected with said pair of plates for providing a signal when at least one metal fragment carried by steam in said conduit means provides a path for electrical conduction between said pair of plates.

6. The erosion detector of claim 5, wherein an end portion of each plate of said pair of plates is flaired mutually away from each other adjacent said upstream location.

7. The erosion detector of claim 6, further comprising permanent magnet means adjoining said pair of plates for providing magnetic guidance of said metal fragment to become located between said pair of plates.

8. The erosion detector of claim 2, wherein said pressure sensor means comprises:

a pressure sensor housing;

a cylinder located within said pressure sensor housing, said conduit means being connected to an upstream end of said cylinder;

a piston located in said pressure sensor housing, said piston being reciprocable within said cylinder; and biasing means connected with said pressure sensor housing for biasing said piston toward said upstream end of said cylinder; and further wherein said signal means comprises:

electrical circuit means connected with said piston and said pressure sensor housing for providing a signal responsive to said piston moving to a predetermined location in said cylinder responsive to steam pressure in said cylinder.

9. The erosion detector of claim 8, wherein said discharge means is connected with said pressure sensor housing far atmospherically venting steam carried in said conduit means.

10. The erosion detector of claim 9, further comprising pressure relief means connected with said discharge means for providing pressure relief in said cylinder by atmospherically venting said steam carried in said conduit means responsive to movement of said piston.

11. The erosion detector of claim 1, wherein said sensor means and said signal means comprise:
a temperature sensor and signal therefor, comprising:
a temperature sensor housing connected with conduit meaner
heat sensitive means located in said temperature housing means for providing predetermined movement in response to changes in temperature of said heat sensitive means caused by heat of steam carried in said conduit means from said detection pipe meaner means for conducting heat of steam carried in said conduit means to said heat sensitive means; and
first electrical circuit means connected with said heat sensitive means for providing a first signal below a predetermined temperature responsive to movement of said heat sensitive means, and for providing a second signal above said predetermined temperature responsive to movement of said heat sensitive means;
a metal fragment sensor and signal therefor, comprising:
a metal fragment sensor housing, said conduit means connecting with said metal fragment sensor at an upstream location and at a downstream location;
a pair of mutually spaced apart and mutually electrically insulated plates located within said fragment sensor housing; and
second electrical circuit means connected with said pair of plates for providing a third signal when at least one metal fragment carried by steam in said conduit means provides a path for electrical conduction between said pair of plates; and
a pressure sensor and signal therefor, comprising:
a pressure sensor housing;
a cylinder located within said pressure sensor housing, said conduit means being connected to an upstream end of said cylinder;
a piston located in said housing, said piston being reciprocable within said cylinder;
biasing means connected with said pressure sensor housing for biasing said piston toward said upstream end of said cylinder; and
third electrical circuit means connected with said piston and said pressure sensor housing for providing a fourth signal responsive to said piston moving to a predetermined location in said cylinder responsive to steam pressure in said cylinder.

12. The erosion detector of claim 11, wherein said discharge means is connected with said pressure sensor housing for atmospherically venting steam carried in said conduit means; and wherein said erosion detector further comprises pressure relief means connected with said discharge means for providing pressure relief in said cylinder by atmospherically venting said steam carried in said conduit means responsive to movement of said piston.

13. The erosion detector of claim 12, wherein an end portion of each plate of said pair of plates is flaired mutually away from each other adjacent said upstream location; and wherein said erosion detector further comprises permanent magnet means adjoining said pair of plates for providing magnetic guidance of said metal fragment to become located between said pair of plates.

14. The erosion detector of claim 13, wherein said heat sensitive means is a bi-metallic strip; said first signal is a green light; and said second signal is a red light.

15. In a boiler apparatus including a feed water vessel; and a feed water steam nozzle, said feed water steam nozzle comprising a pipe having a predetermined length, said feed water steam nozzle having a plurality of mutually spaced apart hole rows, each hole row having a plurality of mutually spaced apart holes along said length, said feed water steam nozzle providing steam through said holes for heating feed water in said feed water vessel; wherein an improvement thereto comprises:
an erosion detector for detecting steam caused erosion of said holes of said feed water steam nozzle and for signaling the detection of steam caused erosion, said erosion detector comprising:
erosion detection pipe means adjoining said feed water steam nozzle for receiving thereinto steam from said feed water steam nozzle, said erosion detection pipe means having a sidewall having a predetermined sensitivity to steam caused erosion, said erosion detection pipe having a predetermined cross-section, a predetermined length and a predetermined cross-sectional shape for locating said sidewall selectively adjacent at least one said hole row, wherein steam is received into said erosion detection pipe means responsive to said sidewall being eroded by the steam;
conduit means connected with said erosion detection pipe means for providing a conduit for steam or steam borne metal fragments from said erosion detection pipe means;
sensor means connected with said conduit means for detecting at least one of steam and steam borne metal fragments in said conduit means to thereby provide detection of steam caused erosion of said sidewall of said erosion detection pipe means; and
signal means connected with said sensor means for providing a signal that steam caused erosion of said sidewall of said erosion detection pipe means has been detected by said sensor means;
wherein the detected steam caused erosion of said sidewall of said erosion detection pipe means is responsive to steam caused erosion of at least one hole of said feed water steam nozzle adjoining said erosion detection pipe means, wherein the detected steam caused erosion of said sidewall of said erosion detection pipe means is such that steam from said feed water steam nozzle enters into said erosion detection pipe means and thereupon passes into said conduit means.

16. The erosion detector of claim 15, wherein said sensor means comprises at least one of three sensor modalities comprising: temperature sensor means for detecting heat of steam carried in said conduit means from said detection pipe means, metal fragment sensor means for detecting metal fragments carried by steam in said conduit means from said detection pipe means, and pressure sensor means for detecting pressure caused by steam carried in said conduit means from said detection pipe means.

17. The erosion detector of claim 15, wherein said sensor means and said signal means comprise:
a temperature sensor and signal therefor, comprising:
a temperature sensor housing connected with said conduit means;

heat sensitive means located in said temperature housing means for providing predetermined movement in response to changes in temperature of said heat sensitive means caused by heat of steam carried in said conduit means from said detection pipe means;

means for conducting heat of steam carried in said conduit means to said heat sensitive means; and first electrical circuit means connected with said heat sensitive means for providing a first signal below a predetermined temperature responsive to movement of said heat sensitive means, and for providing a second signal above said predetermined temperature responsive to movement of said heat sensitive means;

a metal fragment sensor and signal therefor, comprising:

a metal fragment sensor housing, said conduit means connecting with said metal fragment sensor at an upstream location and at a downstream location;

a pair of mutually spaced apart and mutually electrically insulated plates located within said metal fragment sensor housing; and second electrical circuit means connected with said pair of plates for providing a third signal when at least one metal fragment carried by steam in said conduit means provides a path for electrical conduction between said pair of plates; and a pressure sensor and signal therefor, comprising:

a pressure sensor housing;

a cylinder located within said pressure sensor housing, said conduit means being connected to an upstream end of said cylinder;

a piston located in said housing, said piston being reciprocable within said cylinder;

biasing means connected with said pressure sensor housing for biasing said piston toward said upstream end of said cylinder;

steam discharge means connected with said pressure sensor housing for atmospherically venting steam carried in said conduit means;

pressure relief means connected with said steam discharge means for providing pressure relief in said cylinder responsive to movement of said piston; and third electrical circuit mean s connected with said piston and said pressure sensor housing for providing a fourth signal responsive to said piston moving to a predetermined location in said cylinder responsive to steam pressure in said cylinder.

18. The erosion detector of claim 17, wherein said first second and third electrical circuits are mutually electrically connected to thereby comprise a single electrical circuit.

19. The erosion detector of claim 18, wherein an end portion of each plate of said pair of plates is flaired mutually away from each other adjacent said upstream location; and wherein said erosion detector further comprises permanent magnet means adjoining said pair of plates for providing magnetic guidance of said metal fragment to become located between said pair of plates.

20. The erosion detector of claim 19, wherein said heat sensitive means is a bi-metallic strip; said first signal is a green light; and said second signal is a red light.

21. A method for detecting steam caused erosion of a feed water steam nozzle, said feed water steam nozzle comprising a pipe having a predetermined length, said feed water steam nozzle having a plurality of mutually spaced apart hole rows, each hole row having a plurality of mutually spaced apart holes along said length, said feed water steam nozzle providing steam through said holes for heating feed water in said feed water vessel, said method comprising the steps of:

receiving steam from a feed water steam nozzle responsive to a predetermined extent of erosion of at least one hole thereof;

detecting the received steam; and signaling that the received steam has been detected.

22. The method of claim 21, wherein said step of detecting further comprises detecting metal fragments carried by the received steam; and wherein said step of signaling further comprises signaling that the metal fragments carried by the received steam have been detected.

* * * * *